United States Patent [19]

Scheie et al.

[11] 4,437,010
[45] Mar. 13, 1984

[54] METHOD AND APPARATUS FOR ANALYZING CONDITIONER ON A BOWLING LANE SURFACE

[75] Inventors: Carl E. Scheie, Libertyville; G. Arnold Muma, Casnovia, both of Ill.

[73] Assignee: Brunswick Corporation, Skokie, Ill.

[21] Appl. No.: 333,059

[22] Filed: Dec. 21, 1981

[51] Int. Cl.³ .................... F21V 9/16; G01N 21/64
[52] U.S. Cl. ................... 250/459.1; 250/461.1; 250/302; 273/51
[58] Field of Search .............. 250/302, 458.1, 459.1, 250/461.1, 462.1; 273/51

[56] References Cited

U.S. PATENT DOCUMENTS

| | | | |
|---|---|---|---|
| 3,341,705 | 9/1967 | Alburger | 250/302 |
| 3,558,886 | 1/1971 | Carver | 250/461.1 |
| 3,675,015 | 7/1972 | Geib | 250/302 |
| 3,956,630 | 5/1976 | Mellows | 250/461.1 |

*Primary Examiner*—Janice A. Howell
*Attorney, Agent, or Firm*—Wood, Dalton, Phillips, Mason & Rowe

[57] ABSTRACT

A method and apparatus for analyzing and evaluating the thickness and distribution of conditioning material applied to the surface of a bowling lane, wherein the conditioning material is treated with an additive prior to its application to said surface and then the treated conditioning material is transferred from a transverse section of the bowling lane surface onto an elongated strip. The method includes the steps of (1) analyzing the additive transferred onto the elongated strip for providing readings which are proportional to the quantity of lane conditioning material applied to portions of the transverse section of a bowling lane surface, and (2) correlating the readings provided by the analysis with the thickness and distribution of conditioning material applied to the bowling lane surface. The apparatus comprises a mechanism for analyzing the additive transferred onto the elongated strip and for providing readings proportional to the quantity of conditioning material applied to portions of the transverse section of the bowling lane surface. In the preferred embodiment the additive is a fluorescent brightener and the apparatus includes photodiodes which measure the response of the treated conditioning material to ultraviolet light.

5 Claims, 4 Drawing Figures $$V_{OUT} = 10 \frac{V_Z}{V_X}$$

METHOD AND APPARATUS FOR ANALYZING CONDITIONER ON A BOWLING LANE SURFACE

FIELD OF THE INVENTION

The present invention relates generally to a method and apparatus for analyzing and evaluating the profile of a conditioner applied to a bowling lane surface and more particularly to a method and apparatus employing a photovoltaic technique to analyze and evaluate the thickness and distribution of treated conditioning material applied to the surface of a bowling lane.

BACKGROUND OF THE INVENTION

Since bowling lanes are most commonly fabricated of wood or a laminated wood surface, they require daily treatment with an oil based conditioning material to prevent the heat generated by a bowling ball rolling along the bowling lane from scorching the surface thereof. The American Bowling Congress (ABC) requires the conditioner on the lane surface to be of approximately uniform distribution.

Lane conditioning material applied to a bowling lane surface may cause a bowling ball coming in contact with a heavily conditioned segment of the bowling lane to deviate from its normal path of travel. Certain bowling lane proprietors deliberately place a heavy build-up of lane conditioner on the bowling lane to thereby help direct a bowling ball into the pocket (the highest scoring area). Although this technique, known as "lane blocking", is improper, it is used by proprietors because it tends to raise scores above the level which skill alone would determine. By applying lane conditioning material in heavier concentrations at certain segments of the lane, while leaving other segments of the lane conventionally conditioned, a ball can be directed into the strike pocket at the most advantageous angle.

Prior to this invention, the methods used to determine and certify the profile of lane conditioning materials applied to a bowling lane surface were entirely subjective. Another problem with the previous methods of bowling lane certification were their inability to provide for inspection of the lane immediately after a high score had been bowled. And, unless bowling lanes are immediately inspected, proprietors are provided with sufficient time to change the profile of conditioning material before inspection by an ABC official.

It is therefore one object of the present invention to provide an analytical method and apparatus for analyzing and evaluating the thickness and distribution of conditioning material applied to the surface of a bowling lane.

It is another object of the present invention to provide a method and apparatus for determining the profile of oil distribution applied to the surface of a bowling lane by using a photovoltaic measuring technique.

A commonly assigned application, filed simultaneously herewith, and entitled "Method and Apparatus for Transferring Conditioning Material on a Bowling Lane Surface" teaches a method and apparatus for transferring and permanently recording, onto an elongated sample strip, the profile of treated conditioning material applied to a bowling lane surface.

It is yet another object of the present invention to provide a method and apparatus for determining the profile of treated conditioning material applied to the surface of a bowling lane by measuring the response of the treated lane conditioning material transferred onto the sample strip to ultraviolet light.

It is a still further object of the present invention to provide a method and apparatus for determining the profile of treated conditioning material applied to the surface of a bowling lane by using a photovoltaic measuring technique which analyzes the response of a fluorescent additive with which the conditioning material is treated to ultraviolet light and correlates that response to the thickness and distribution of treated conditioning material applied to said lane surface.

These and other features of the present invention will become readily apparent to one of ordinary skill in the art when read in conjunction with the detailed description of the drawings and the claims which follow.

BRIEF SUMMARY OF THE INVENTION

Disclosed herein is a method and apparatus for analyzing and evaluating the thickness and distribution of treated conditioning material applied to the surface of a bowling lane. By treating the lane conditioning material with a fluorescent additive, the conditioning material radiates a bright blue color under ultraviolet light. The intensity of the radiated color varies in proportion to the thickness and distribution of treated conditioning material on the bowling lane surface.

When the profile of conditioning material applied to the bowling lane surface is to be analyzed, an elongated absorbent sample strip is placed across the bowling lane to transfer treated conditioning material from the bowling lane surface. Upon removal from the bowling lane surface, the sample strip provides a permanent record of the profile of said lane conditioning material.

In accordance with the objectives of the present invention, the sample strip is exposed to a source of ultraviolet light. Since variations in the thickness of conditioner transferred onto the sample strip are reflected by corresponding variations is intensity of light detected by a photocell, the output voltage of the photocell is measured to provide a reading which can then be correlated with the thickness of conditioner applied to the surface of the bowling lane.

The apparatus includes a source adapted to direct ultraviolet light onto the treated conditioning material transferred onto the sample strip. The intensity of light from the treated conditioning material is monitored as output voltage of the photocell at prescribed intervals along the length of the strip, and the values thereof are plotted relative to the positions across the bowling lane surface from which the particular section of treated conditioning material was analyzed. The resulting graph depicts the thickness and distribution of treated conditioning material across a selected transverse section of the bowling lane surface.

Although not specifically described, it should be apparent that the lane conditioning material could be formulated with a metal, optionally active or magnetic additive instead of the fluorescent additive described herein. The metal, optically active or magnetic additive could then be analyzed using metallic, polarized or magnetic detection equipment. Further, although photovoltaic equipment is described herein as the preferred apparatus for evaluating the lane conditioning material sample, it should be obvious that other types of evaluation apparatus such as a fluorescent or an infra-red spectrometer could be employed without departing from the spirit and scope of the present invention. It must therefore be realized that the purpose of the present invention is to analyze and evaluate the thickness and distribution of treated conditioning material applied in the surface of a bowling lane. Whether that objective is accomplished with magnetic, optically active or metallic additives, it is the concept of analyzing the treated conditioning material sample and correlating that analysis to the profile of conditioning material on the bowling lane surface which forms the basis for this invention.

DETAILED DESCRIPTION OF THE DRAWINGS

Generally, the purpose of the present invention is to provide a method and apparatus for analyzing an elongated sample strip having transferred thereonto treated lane conditioning material from a transverse section of the surface of a bowling lane. The sample strip is described in a patent application filed simultaneously herewith, of common assignee and entitled "Method and Apparatus for Transferring Conditioning Material on a Bowling Lane Surface." The sample strip is a transparent, multi-layered tape having the treated lane conditioning material permanently sealed between an absorbent strip layer and a polyurethane backing strip layer.

The material for conditioning the bowling lane may be chosen from any of the well known, oil-based dressing such as BRUNSWICK GOLDEN (Trademark) Lane Conditioner. In the preferred embodiment, the conditioner is treated with a fluorescent brightness, such as UVITEX OB, a registered trademark of the Ciba-Geigy Corp. of Ardsley, N.Y. UVITEX OB (Registered) is a bis (benzoxazolyl) derivative with a melting range of 197-203 degrees C. and a yellow or yellow-green crystalline appearance.

The UVITEX OB (Registered) additive was selected to be uniformly mixed with the conditioning material because the additive, when transferred from the surface of the bowling lane and exposed to ultraviolet light, emits light-blue visible light, with the intensity thereof varying in proportion to the thickness of the treated conditioning material transferred from the bowling lane surface. Further, while the UVITEX OB (Registered) additive has a maximum absorption of invisible ultraviolet light at a wavelength of 375 nanometers, it emits the most visible blue light at a wavelength of 435 nanometers. It was therefore, determined the visible light emitted by the sample strip, after excitation by the ultraviolet light, could be quantitatively measured and that measurement could then be correlated to the thickness and distribution of treated conditioning material on the surface of a bowling lane by using calibration data from known conditioning material thicknesses.

Figure 1:
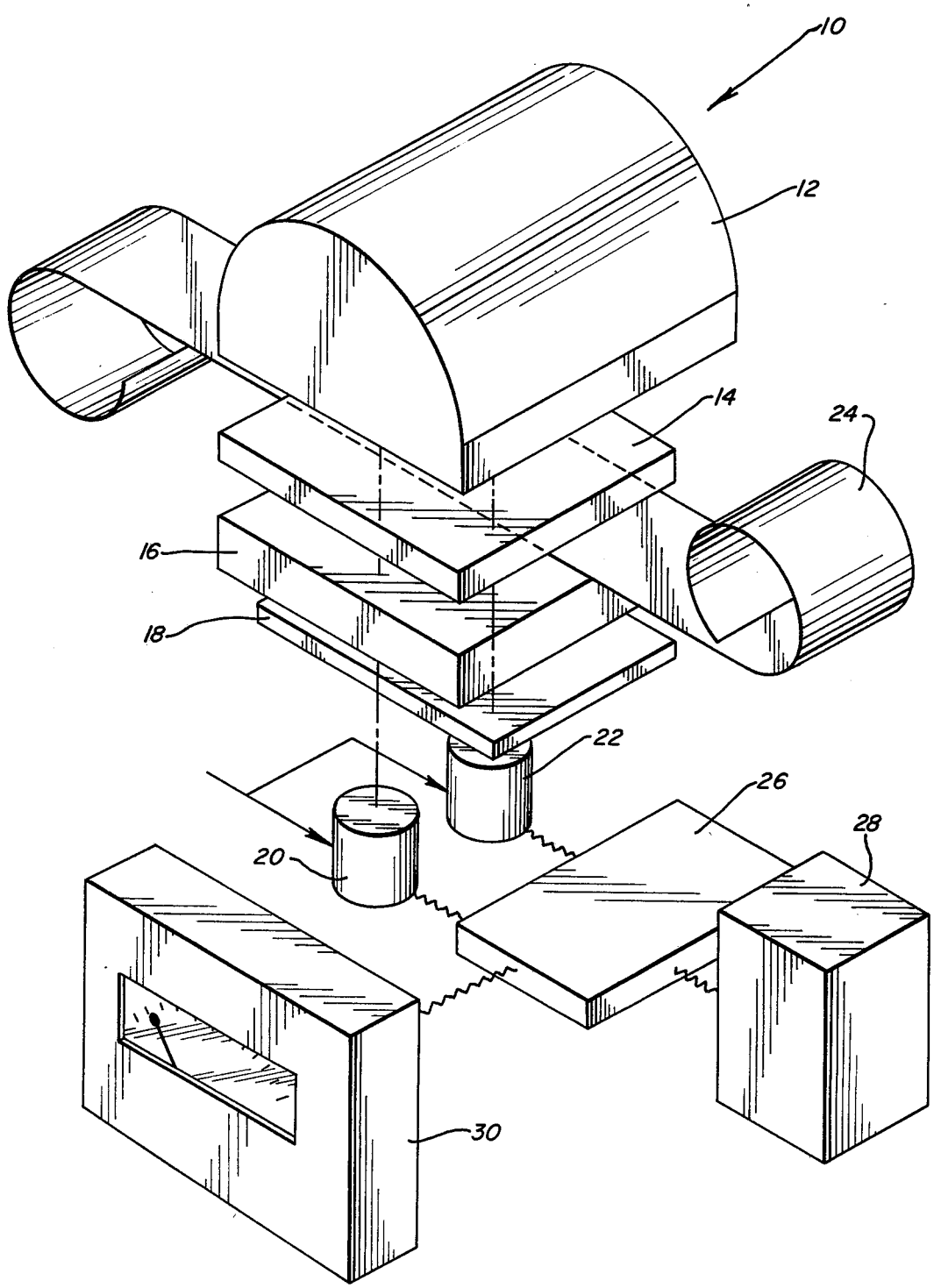
FIG. 1 is an exploded perspective view illustrating the apparatus of the present invention as operatively positioned to analyze a sample of treated lane conditioning material.

In view of the foregoing background, reference is now made to the drawings, and particularly to FIG. 1, wherein the apparatus for analyzing treated lane conditioning material applied to a section of a bowling lane surface is shown generally by the reference numeral 10. The apparatus includes a source of ultraviolet light 12, a filter 14 for absorbing visible light from the source 12, a fluorentine glass plate 16 for averaging minor variations in conditioning material thicknesses, a filter 18 for absorbing ultraviolet light from the additive on the sample strip, a reference photocell 20 for measuring the intensity of light from the source 12, a photocell 22 for measuring the intensity of light from the treated conditioning material sample 24, a divider circuit 26 for relating the intensity of light sensed by the reference photocell 20 to the intensity of light sensed by the conditioning material photocell 22, a power source 28, such as a DC battery, for energizing the photocells, and a voltmeter 30 for measuring the intensity of light sensed by the conditioning material photocell 22 relative to the intensity of light sensed by the reference photocell 20.

The source of ultraviolet light 12 may be any ultraviolet lamp which emits long wavelength (295-430 nanometer) ultraviolet light. The model UVSL 21 Lamp manufactured by Ultraviolet Products is the preferred source of light because of its maximum emittance of about 365 nanometers.

While the model UVSL 21 source of ultraviolet light emits the preferred wavelength, the intensity of emitted light tends to decay with time. This results in a decrease in the light emitted by the sample strip during tests over several minutes in duration. It is therefore desirable that readings measured by a photocell be normalized to prevent fluctuation of the readings due to a loss of intensity caused by the passage of time.

The reference photocell 20 and the conditioning material photocell 22 are preferrably photodiodes produced by United Detector Technology, Inc. These photodiodes (1) provide a voltage output proportional to the intensity of incident visible light, (2) detect light wavelengths of 300-400 nanometers and (3) are most efficient at wavelengths of approximately 385 nanometers.

Since the sample of ultraviolet conditioning material emits visible blue light in an intensity proportional to the sample thickness, the conditioning material photocell 22 detects the varying intensity, and the relative thickness of the conditioning material can be correlated to the detected intensity.

However, simply placing the sample strip of conditioning material 24 between the source of ultraviolet light 12 and the conditioning material photocell 22 will not provide accurate readings of light intensity because even the lowest intensity light emitted from the source 12 saturates the conditioning material photocell 22, thereby preventing it from distinguishing between the different fluorescent intensities emitted by the treated conditioning material on the sample strip 24.

To prevent photocell saturation, light filters are positioned between the source 12 and the conditioning material photocell 22. Since only ultraviolet light is useful in activating the treated conditioning material on the sample strip 24, an exciter filter 14 for absorbing light outside of the desired 300-400 nanometer ultraviolet light wavelength range, such as Kodak Wratten 18A, is placed between the source of ultraviolet light 12 and the sample strip 24. This exciter filter 14 isolates the reading of the conditioning material photocell 22 from the influence of visible light from the source 12. It only being necessary that the conditioning material photocell 22 detect the visible blue light emitted by the treated conditioning material on the sample strip 24, a barrier filter 18 for absorbing all but the desired visible wavelength (420 nanometers and up) light is positioned between the sample strip 24 and the conditioning material photocell 22. Without the barrier filter 18, ultraviolet light from the source 12 would saturate the conditioning material photocell 22.

Figure 2A:
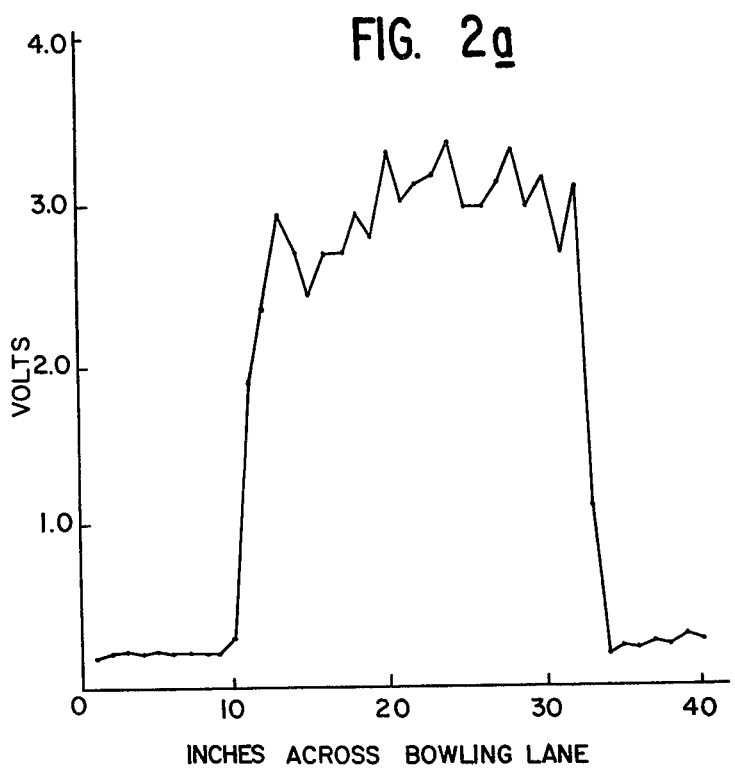
FIG. 2a is a graph of voltage versus inches across a bowling lane surface showing the configuration of a blocked lane as measured by the photovoltaic technique described by the present invention.
Figure 2B:
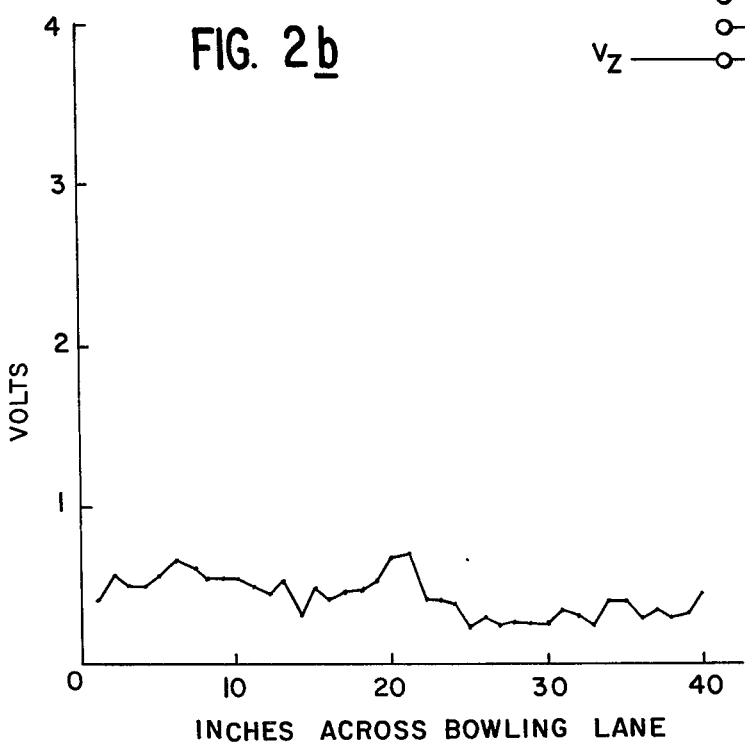
FIG. 2b is a graph of voltage versus inches across a bowling lane surface showing the configuration of a normally conditioned lane as measured by the photovoltaic technique described by the present invention.

By measuring the visible emittance at regular intervals along the conditioning material sample strip 24 and graphing the normalized voltage output versus distance across the width of the bowling lane, the thickness and distribution of conditioning material applied to that bowling lane surface can be plotted. FIG. 2a illustrates the profile of conditioning material as measured by the apparatus 10 and reveals a heavy concentration of conditioning material applied in the central portion of the bowling lane surface. The heavy concentration of conditioning material represents a blocked lane condition which would not be sanctioned by the ABC. FIG. 2b is a graph plotted from measurements sensed by the apparatus 10 which reveals a uniform concentration of conditioning material applied across the transverse surface of the bowling lane. The uniform concentration of conditioning material represented by the graph of FIG. 2b would meet ABC specifications.

From the plot of FIG. 2b, it is apparent the thickness of conditioning material varies intermittently, even across finite segments of a bowling lane surface. Peaks and valleys in conditioning material thickness occur within the one inch intervals defined by the boards which form the bowling lane surface. This causes the measured output of the apparatus 10 to vary correspondingly.

To elimate most of the intermittent variances in conditioning material thickness readings, a fluorentine glass plate 16 is placed between the sample strip 24 and the barrier filter 18. The randomly-faceted surfaces of the plate 16 transmit the average intensity of light from the treated conditioning material on the sample strip 24. The result is a single data point for each of the 42 one inch boards which form the bowling lane surface. In other words, the glass plate 16 operates to provide an average thickness of treated conditioning material for measurement by the photocells. Therefore, a graph drawn from measurements of light after it has passed through the fluorentine glass plate 16, provides a smooth plot of conditioning material thickness.

As discussed hereinbefore, the decay in intensity of the source of ultraviolet light 12 results in the output voltage measured by the photocells to decrease with time. It is therefore desirable to use some mechanism such as a divider circuit 26 (provided by modual divider 434A sold by Analog Devices, Inc.) to eliminate this variable. The divider circuit 26 receives input voltage readings from the conditioning material photocell 22 and the reference photocell 20 and, in accordance with the transfer function of the divider circuit 26, provides an output voltage signal which represent a ratio of the two input voltages. Since the intensity of light received by photocell 20 or 22 varies with the intensity of light from the source 12, fluctuations in intensity of light from the source affects both photocells proportionately. Therefore, the divider circuit 26 normalizes the measurements of voltage output from the conditioning material photocell 22.

Figure 3:
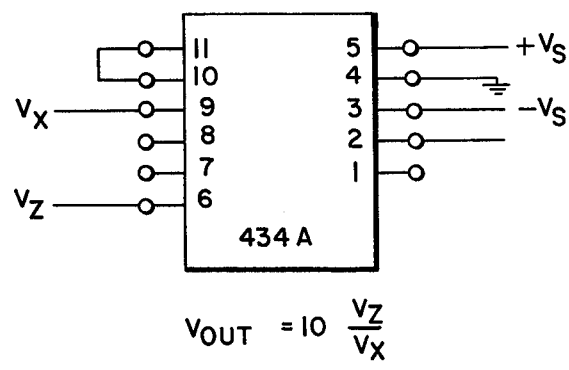
FIG. 3 is a schematic drawing of a modual divider circuit diagram.

FIG. 3 shows a schematic diagram of functional module 434A as operatively connected for providing a ratio of the output voltage of the two photocells. The module receives a voltage signal from the conditioning material photocell 22 and the reference photocell 20 and establishes the ratio of conditioning material voltage, $V_x$, to the reference voltage, $V_z$. The divider circuit 26 may also be an Ic chip or its digital equivalent. The output voltage of the divider ciruit 26 can be read on the voltmeter 30 as Vout. The voltmeter 30 is preferably digital, although any instrument relying on input voltage signals could be used. As the sample strip 24 is fed through the apparatus 10, the operator simply records the reading apparatus on the digital display of the voltmeter 30.

While the preferred form of the invention has been described in detail, various changes could be made in the apparatus and method without departing from the spirit and scope of the invention. It is therefore intended that all matter contained in the above description and shown in the accompanying drawings shall be interpreted as illustrative and not in a limiting sense.

What I claim and desire to be secured by Letters Patent of the United States is:

1. Apparatus for analyzing and evaluating the thickness and distribution of conditioning material applied to the surface of a bowling lane, the conditioning material treated with a fluorescent additive prior to application to the bowling lane surface, the apparatus adapted for analyzing the treated conditioning material which has been transferred onto an elongated transparent strip from a transverse section of the bowling lane surface;

the apparatus comprising, in combination:
a source of ultra-violet light directed to strike one side of the elongated strip;
a first photocell on the side of the strip opposite the one side for sensing blue light emitted by the fluorescent additive;
a second photocell adapted to receive light emanating from the source; and
means for comparing the intensity of light from the strip measured by the first photocell with the intensity of the light from the source measured by the second photocell whereby readings of intensity of light from the strip can be measured independently of variations in intensity of light from the source,
said light intensity from the strip being directly proportional to the quantity of conditioning material applied to finite portions of the transverse section of a bowling lane surface and correlated to the thickness and distribution of conditioning material transferred from the bowling lane surface.

2. Apparatus as in claim 1 further including a first filter adapted to absorb visible light directed from the source of ultra-violet light to the strip and a second filter adapted to absorb ultra-violet light directed from the strip to the first photocell.

3. Apparatus as in claim 2 further including a fluorentine glass plate positioned between the strip and the second filter for transmitting to the first photocell the average intensity of light impinging thereon.

4. Apparatus as in claim 3 wherein the comparing means is a divider circuit adapted to measure the ratio of the intensity of light from the strip to the intensity of light emanating from the source.

5. A method of analyzing and evaluating the thickness and distribution of bowling lane conditioning material applied to the surface of a bowling lane;

the treated conditioning material transferred from a transverse section of the bowling lane surface onto an elongated strip;

the method including the steps of:

directing a source of ultra-violet light onto the treated conditioning material on the elongated strip;

using a first photocell to measure the intensity of visible light from the additive on the elongated strip;

using a second photocell to measure the intensity of light emanating from the source;

comparing the intensity of light from the strip measured by the first photocell with the intensity of light from the source measured by the second photocell, whereby the intensity of light from the strip can be measured independently of variations in intensity of light from the source;

analyzing the additive transferred onto the elongated strip by determining the intensity of light from the strip, which is proportional to the quantity of conditioning material applied to finite sections of a bowling lane surface; and correlating the readings provided by the analysis with the thickness and distribution of conditioning material applied to the bowling lane surface.

* * * * *